(12) United States Patent
Wiesner et al.

(10) Patent No.: US 8,409,876 B2
(45) Date of Patent: *Apr. 2, 2013

(54) FLUORESCENT SILICA-BASED NANOPARTICLES

(75) Inventors: Ulrich B. Wiesner, Ithaca, NY (US); Hooisweng Ow, Arlington, MA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/579,302

(22) Filed: Oct. 14, 2009

(65) Prior Publication Data
US 2010/0035365 A1    Feb. 11, 2010

Related U.S. Application Data

(63) Continuation of application No. 10/306,614, filed on Nov. 26, 2002, now abandoned.

(51) Int. Cl.
*G01N 33/551* (2006.01)
*B32B 19/00* (2006.01)

(52) U.S. Cl. .......................... 436/524; 977/904; 428/144

(58) Field of Classification Search .................. None
See application file for complete search history.

(56) References Cited

U.S. PATENT DOCUMENTS
2003/0124564 A1 * 7/2003 Trau et al. .......................... 435/6

FOREIGN PATENT DOCUMENTS
| WO | WO 00/32542 | * | 6/2000 |
| WO | WO 00/67027 | * | 11/2000 |
| WO | WO-0188540 | | 11/2001 |

OTHER PUBLICATIONS

Melde et al., Chem. Mater. vol. 11: 3302-3308; 1999.*
Van Blaaderen et al., Langmuir, vol. 8: 29212931; 1992.*
Miyoshi, Hirokazu, Silica Nanoparticles Containing High-Brightness Fluorescent Dye Molecules, an English translation of Hirokazu Miyoshi, Koukido Keikou Shikiso Bunshi Ganyuu Silica Nanobiryuushi High Fluorescein Molecular Containing Silica Nanoparticle, STEP Network, vol. 8, No. 1, pp. 4-5, Apr. 2002 (6 pgs.).
Japanese Patent Office, Notice of Rejection in Japanese Application No. 2004-566499, dated Sep. 7, 2010 (11 pgs.).
Hirokazu Miyoshi, Koukido Keikou Shikiso Bunshi Ganyuu Silica Nanobiryuushi (High Fluorescein Molecular Containing Silica Nanoparticle, STEP Network, vol. 8, No. 1, pp. 4-5, Apr. 2002 (2 pgs.).
A. Imhof et al., Spectroscopy of Fluorescein (FITC) Dyed Colloidal Silica Spheres, J. Phys. Chem. B, vol. 103, pp. 1408-1415, 1999 (8 pgs.).
Nynke A. M. Verhaegh et al., Dispersions of Rhodamine-Labeled Silica Spheres: Synthesis, Characterization, and Fluorescence Confocal Scanning Laser Microscopy, Langmuir, vol. 10, No. 5, pp. 1427-1438, 1994, (12 pgs.).
European Search Report for European Patent Application No. EP 11 15 6074 dated Oct. 24, 2011 (11 pages).
Ruxiong Cai et al., "Photokilling of Malignant Cells with Ultrafine $TiO_2$ Powder", 1991 Bull. Chem. Soc. Jpn, 64 (pp. 1268-1273).
Rovelyn Tapec et al., "Development of Organic Dye-Doped Silica Nanoparticles for Bioanalysis and Biosensors", 2002 J. Nanosci. Nanotech. vol. 2, No. 3/4 (pp. 405-409).
Andrew Burns et al., "Fluorescent core-shell silica nanoparticles: towards "Lab on a Particle" architectures for nanobiotechnology", 2006 Chem. Soc. Rev. 35 (pp. 1028-1042).
Jason E. Fuller et al., "Intracellular delivery of core-shell fluorescent silica nanoparticles", 2008 Biomaterials 29 (pp. 1526-1532).

* cited by examiner

*Primary Examiner* — Shafiqul Haq
*Assistant Examiner* — Galina Yakovleva
(74) *Attorney, Agent, or Firm* — Harris Beach PLLC (57) ABSTRACT

The present invention provides nanoparticle compositions comprising, for example, a core comprising a fluorescent silane compound; and a silica shell on the core. Also provided are methods for the preparation of nanoparticle compositions including fluorescent nanoparticles, ligated-fluorescent nanoparticles, ligated-fluorescent nanoparticles having therapeutic agents, and ligated-fluorescent nanoparticles coupled or associated with an analyte. Also provided are methods: for the detection of the ligated-fluorescent nanoparticles; for associating the linked-fluorescent nanoparticles with a cellular component of interest and recording or monitoring the movement of the cellular component; for improving the therapeutic properties of the therapeutic agent by combining the therapeutic agent with linked-fluorescent nanoparticles and contacting or administering the combination to a cell or organism; for making and using the fluorescent nanoparticles in, for example, diagnostic agents for the detection of various analytes, and like applications.

10 Claims, 3 Drawing Sheets

FLUORESCENT SILICA-BASED NANOPARTICLES

CROSS-REFERENCE TO RELATED APPLICATIONS

This application is a continuation application of U.S. patent application Ser. No. 10/306,614, filed Nov. 26, 2002, now abandoned.

FIELD OF THE INVENTION

The invention generally relates to nanoparticles, and more specifically to ligated-fluorescent nanoparticles, methods of making ligated-fluorescent nanoparticles, and methods of using the ligated-fluorescent nanoparticles as biomarkers to, for example, monitor the motion or movement of cellular components on or within cell systems, and for the detection, diagnosis, or treatment of diseases or conditions, for example in intact or living cells.

BACKGROUND OF THE INVENTION

Fluorescent and magnetic polymeric particles have known utility as markers and indicators in various biomedical assays. Among the most commonly used markers for sorting cells are immunoconjugates or immunological labels which include, for example, immuno-fluorescent and immuno-magnetic labels. Immuno-fluorescent labels typically include, for example, a fluorescent molecule joined to an antibody. Immuno-magnetic labels typically include, for example, a superparamagnetic particle joined to either a primary or secondary antibody. Cell labeling can be performed by, for example, attaching the antibody to a marker of interest (e.g., receptor site) on the surface of the cell, that is, a cell surface marker. However, the chemical and physical structure of cell surface marker and density of immunological labels attached to the cell surface have generally been difficult to accurately determine.

Fluorescent labels have been prepared, for example, by embedding or covalently coupling a fluorescent dye onto a polymeric particle. The resulting fluorescent microparticles can be analyzed manually or by other methods known in the art but preferably using an automated technique, e.g., flow cytometry, such as disclosed in U.S. Pat. No. 4,665,024, to Mansour, et al. The versatility of the fluorescent particles can be further enhanced by the incorporation of multiple fluorescent materials in a single particle. However, while simple absorption of a single dye into a particle can be adequate for most purposes, problems can arise when more than one dye is absorbed into a particle, including: inconsistent emissions attributable to, for example, intermolecular fluorescent energy transfer; differential fluorophore uptake ratios attributable to different dye solubilities within the polymeric matrix; and substrate induced changes in either or both the absorption and emission spectrum of the intercalated fluorophore.

Magnetic particles, such as known magnetically active materials, can be bonded or attached to, for example, antibodies, such as, monoclonal antibodies that are specific to a particular cell type, antigen, or other targets. The resulting magnetic-antibodies can then be mixed with a large population of many different cell types, for example, crude tissue samples, cells grown in a reactor, and the like. The magnetic-antibodies therefore attach only to their pre-selected target cell type, forming a magnetic-antibody-cell conjugate. The conjugate can then be separated from the rest of the cell population using a magnetic field. A shortcoming of magnetic particles is the lack of specificity in magnetic labeling in that a cell or other biological target analyte may be rendered paramagnetic by a number of different routes which can confound the analysis and diagnostic information afforded by the method, for example, by binding a specific paramagnetic compound to a specific hapten on a cell or by specific or non-specific binding of a paramagnetic metal or metal complex directly to a cell, such as, a metal binding microorganism or by phagocytosis. Other problems encountered with magnetic particles used in detection and diagnostics include, for example, difficulty in obtaining highly accurate quantification of a cell population's magnetic susceptibility. In addition to their magnetic properties (i.e. magnetic, paramagnetic, and superparamagnetic) magnetic-antibodies can be classified, for example, into three broad categories based on their relative descending particle size: magnetic particulate labels, colloidal magnetic labels, and molecular magnetic labels, see for example U.S. Pat. No. 6,412,359.

Latex nanoparticles having a polymeric core and a surface decorated with, for example, a ligand molecule capable of specific binding with a cell surface and optionally decorated with genetic material, such as a mutant gene, are known and may have utility in, for example, gene delivery to a cell and expression therein, for disrupting tumors, and related treatment applications, see for example, *Science*, 296, 2404 (2002).

Optically active nanoparticles, such as fluorescent nanoparticles, having an electrically conducting shell and a silica core are known and have utility in, for example, modulated delivery of a chemical and treatment applications, see for example, U.S. Pat. Nos. 6,344,272, and 6,428,811.

A shortcoming of existing fluorescent probe nanoparticles is their limited brightness and their attenuated detectability as fluorescent probes in dispersed systems, particularly with single fluorescent nanoparticles.

There is currently a need for improved fluorescent nanoparticles and methods for detection and analysis therewith, including their use as fluorescent markers or probes in dispersed biological media.

SUMMARY OF THE INVENTION

The invention provides a fluorescent nanoparticle comprising: a core comprising a fluorescent silane compound; and a silica shell on the core.

The invention also provides a fluorescent nanoparticle comprising:

a core comprising a fluorescent silane compound; and a porous silica shell on the core.

The invention also provides a fluorescent nanoparticle which can further include a ligand, such as a antibody, conjugated with or coated on the surface of the fluorescent nanoparticle to form a ligated-fluorescent nanoparticle. The ligated- or ligand bearing-fluorescent nanoparticles of the present invention can be used, for example, as highly target specific diagnostic agents, and motion monitoring agents when combined with cells or cell components.

The invention also provides a pharmaceutical carrier or drug delivery vehicle comprising the fluorescent nanoparticles or the ligated-fluorescent nanoparticles of the present invention.

The invention also provides a fluorescent imaging agent comprising the ligated-fluorescent nanoparticles of the present invention.

The invention also provides ligated-fluorescent nanoparticles as pharmaceutical carrier particles. Thus, the ligated-fluorescent nanoparticles can further include a therapeutic agent, which therapeutic agent is on the surface or is conjugated with the surface of the fluorescent nanoparticle to form a pharmaceutical composition.

The invention also provides a method of making a fluorescent nanoparticle comprising:

mixing a fluorescent compound, such as a reactive fluorescent dye, and an organo-silane compound, such as a co-reactive organo-silane compound, to form a fluorescent core; and mixing the resulting core with a silica forming compound, such as a tetraalkoxysilane, to form a silica shell on the core.

The invention also provides a method for monitoring movement of a cellular component of a cell comprising:

contacting the cell with a ligated-fluorescent nanoparticle to form a cell selectively decorated with the ligated-fluorescent nanoparticle; and recording the motion of a fluorescent loci for a time.

The invention also provides a method for treating disease comprising:

administering to a patient in need of treatment with an effective amount of a ligated-fluorescent nanoparticle, which nanoparticle optionally includes a therapeutic agent, the nanoparticle being adapted to selectively associate with a disease producing component of the cell, to form a selectively decorated cell with the ligated-fluorescent nanoparticle; and illuminating the decorated cell.

The invention also provides a method for treatment comprising:

contacting a cell with a ligated-fluorescent nanoparticle, which nanoparticle optionally includes a therapeutic agent, to form a cell selectively decorated with the ligated-fluorescent nanoparticle; and irradiating the resulting decorated cell for a time.

The invention also provides a kit for use in the detection of an analyte, the kit comprising a ligated-fluorescent nanoparticle, as illustrated herein.

The invention also provides a kit for detecting and monitoring a cell surface component comprising a ligated-fluorescent nanoparticle for detecting the cell surface component, and optionally a recorder for monitoring the cell surface component.

The invention also provides an assay method for detecting motion or a change in the location of a cellular component in, or on the surface of, a cell when the cell is treated with a therapeutic agent comprising:

contacting a cell with a ligated-fluorescent nanoparticle, wherein the nanoparticle includes a therapeutic agent, to bind the ligated-fluorescent nanoparticle to a cellular component; and recording the fluorescent signal.

DETAILED DESCRIPTION OF THE INVENTION

Applicants have discovered fluorescent nanoparticles, and linked- or ligated-fluorescent nanoparticles of the invention that are useful for labeling, detection, identification, motion monitoring, and like applications, of various biological and non-biological analytes. The linked- or ligated-fluorescent nanoparticles of the invention can also be useful in therapeutic treatment, when used as a pharmaceutical carriers, for example, in combination with a suitable therapeutic agent.

The present invention provides nanoparticles which can have useful multifunctional architectures, for example, a fluorescent nano-sized core which can optionally contain other functionality such as a magnetic component, a silica shell which can be made to have a range of useful thicknesses and surface properties, such as a smooth monolithic surface or a highly porous surface, and which silica surface can be further physically or chemically modified with, for example, a ligand or a therapeutic agent.

The present invention provides for the preparation and characterizations of fluorescent nanoparticles in various sizes suitable for single particle tracking (SPT) applications. Nanoparticles of various diameters can be prepared having narrow size distributions. The versatility of the preparative route allows for the incorporation of different fluorescent materials, such as dyes, depending on the intended nanoparticle application. Methods for surface functionalization are also provided which enable the conjugation of specific ligands, such as antibodies or proteins, onto the fluorescent nanoparticles to form probes useful for specific SPT experiments. The nanoparticle preparative procedure enables the preparation, by in situ systematic nanoparticle size-growth, of fluorescent nanoparticles in the range of, for example, from about 10 to about 500 nm, and from about 25 to about 100 nm, and narrower ranges therein as illustrated herein.

The fluorescent nanoparticles can be conjugated with a molecule or entity, such as an antibody ligand or linker, to provide a linked- or ligated-fluorescent nanoparticle which can be used to identify, detect, target (i.e. pinpoint or specify with a high level of certainty), monitor, or modify a disease state or condition, such as the presence or absence of particular receptors, metabolic levels of particular receptors, and like components. The linked- or ligated-fluorescent nanoparticle can be still further conjugated or associated with, for example, a therapeutic agent and used to, for example, treat a disease state or condition, such as by delivering the therapeutic agent to a diseased site in a highly specific or localized manner and in a relatively high concentration with release of the therapeutic agent in a relatively controlled manner. The ligated-fluorescent nanoparticles can be used for directed delivery of a therapeutic agent to a desired location in a variety of systems, such as on, or within, a cell or cell component, or within the body of an organism, such as a human, e.g. across the blood-brain barrier.

In embodiments the therapeutic agent can be either or both absorbed into, such as the interstices or pores of the silica shell, or coated onto the silica shell of the fluorescent nanoparticle. In other embodiments where the silica shell is incomplete, the therapeutic agent can be associated with the fluorescent core, such as by physical absorption or by bonding interaction. The therapeutic agent can also be associated with the ligand of a ligated-fluorescent nanoparticle if desired.

The ligated-fluorescent nanoparticles of the present invention can be used in a variety of diagnostic and treatment applications, for example, as a pharmaceutical carrier for therapeutic agents, and as a fluorescent marker in, for example, single nucleotide polymorphism (SNPs) experiments, such as where a DNA sample is stained with a fluorescent marker and gene activity can be detected as a colored glow of the marker when illuminated with a laser.

The nanoparticles of the invention, alone or in combination with a ligand, can be used for passive or covalent coupling of biological material, i.e. an analyte, such as haptens, antigens, antibodies, enzymes or nucleic acids, and used for various types of analyte assays such as immunoassays, nucleic acid (DNA or RNA) assays, affinity purification, cell separation, and other medical, diagnostic, environmental, and industrial applications. The nanoparticles incorporate known fluorescently responsive materials, such as, dyes, pigments, or combinations thereof. A wide variety of suitable chemically reactive fluorescent dyes are known, see for example MOLECULAR PROBES HANDBOOK OF FLUORESCENT PROBES AND RESEARCH CHEMICALS, $6^{th}$ ed., R. P. Haugland, ed. (1996). A typical fluorophore is, for example, a fluorescent aromatic or heteroaromatic compound such as is a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a coumarin (including hydroxycoumarins and aminocoumarins and fluorinated derivatives thereof), and like compounds, see for example U.S. Pat. Nos. 5,830,912; 4,774,339; 5,187,288; 5,248,782; 5,274,113; 5,433,896; 4,810,636; and 4,812,409.

The co-reactive organosilane used for forming the fluorescent core has the general formula $R_{(4-n)}SiX_n$, where X can be a hydrolyzable group such as ethoxy, methoxy, or 2-methoxyethoxy; R can be a monovalent organic radical of from 1 to 12 carbon atoms which can optionally contains a functional organic group such as mercapto, epoxy, acrylyl, methacrylyl, or amino; and n is an integer of from 0 to 4. The co-reactive organosilane used for forming the fluorescent core preferably has n equal to 3. A organosilane used for forming the silica shell has n equal to 4. The use of functional mono-, bis- and tris-alkoxysilanes for coupling and modification of co-reactive functional groups or hydroxy-functional surfaces, including glass surfaces, is also known, see Kirk-Othmer, Encyclopedia of Chemical Technology, Vol. 20, 3rd Ed., J. Wiley, N.Y. Although not desired to be limited by theory, the coupling arises as a result of hydrolysis of the alkoxysilane groups to silanol groups and as a result of condensation with hydroxyl groups of the surface, see E. Pluedemann, Silane Coupling Agents, Plenum Press, N.Y. 1982. Thus, the above mentioned organo-silane compounds and like coupling agents can be used: to make the core; to make the silica shell, to modify the surface of the resulting silica shell coated fluorescent core nanoparticles; to attach or couple a ligand to the fluorescent nanoparticles; or to modify the properties of ligand before or after attachment to fluorescent nanoparticle. The organo-silane can cause gels, so it may be desirable to employ an alcohol or other known stabilizers. When the organo-silane is to be co-polymerized with another monomer such as a reactive fluorescent compound, a stabilizer can be selected that does not interfere with the polymerization. An alcohol, such as methanol, is especially useful and can be employed in amounts, for example, from about twice to about ten times the amount of the organo-silane.

The nanoparticles can optionally incorporate known magnet or magnetically responsive materials, such as, superparamagnetic, paramagnetic, ferromagnetic metal oxide, and combinations thereof.

The fluorescent nanoparticles of the present invention comprise a core comprising a fluorescent silane compound; and a silica shell on the core. The core of the nanoparticle can comprise, for example, the reaction product of a reactive fluorescent compound and an co-reactive organo-silane compound, and the shell can comprise, for example, the reaction product of a silica forming compound. The silica forming compound can produce, for example, one or more layers of silica, such as from 1 to about 20 layers, and depending upon the shell characteristics desired, such as shell layer thickness, the ratio of the shell thickness to the core thickness or diameter, silica shell surface coverage of the core, porosity and carrying capacity of the silica shell, and like considerations.

The silica shell coating on the core can cover, for example, from about 10 to about 100 percent of the surface area of the core. The ligand when ligated on the surface of the fluorescent nanoparticle can cover, for example, from about 0.1 to about 100 percent of the surface area of the core. The thickness or diameter of the core to the thickness of the silica shell can be in a ratio of, for example, from about 1:1 to about 1:100. The diameter of the fluorescent nanoparticle can be, for example, from about 1 to about 1,000 nanometers. The diameter of a ligated-fluorescent nanoparticle can be comparable to or larger than the diameter of the fluorescent nanoparticle depending upon, for example, the size and the amount of the ligand selected. In embodiments the diameter of the core can be, for example, from about 10 to about 300 nanometers, and preferably from about 25 to about 200 nanometers, and the thickness of the silica shell can be, for example, from about 25 to about 800 nanometers, and preferably from about 25 to about 500 nanometers. In preferred embodiments, such as when the nanoparticles are selected as a carriers, the silica shell is made porous to accommodate for example a therapeutic agent, and as illustrated herein. More preferably the nanoparticles The preparative methods for fluorescent nanoparticles of the present invention can yield nanoparticles, for example, of about an order of magnitude smaller in size than those reported by van Blaaderen and Vri, *Langmuir*, 8, 2921-2925 (1992) (monodisperse silica sphere core particles coated with dyes and further encapsulated with silica). The silica shell can be either solid, that is relatively non-porous, or meso-porous, such as semi-porous. The silica shell of the fluorescent nanoparticles is preferably dielectric. The silica shell of the fluorescent nanoparticles can be adapted to function as a pharmaceutical carrier nanoparticle, that is made to contain, for example, therapeutic agents, such as drugs or proteins for transport and delivery of in vivo or in vitro. Thus, the fluorescent nanoparticles of the present invention can provide a pharmaceutical carrier system which can be adapted for controlled delivery or release of therapeutic agents.

In embodiments, a ligand placed on the surface of the fluorescent nanoparticle forms a ligated-fluorescent nanoparticle. The placement of the ligand can be accomplished, for example, by attachment with a covalent bond or by physical absorption. The ligand on the surface of the fluorescent nanoparticle can be, for example, a biopolymer, a synthetic polymer, an antigen, an antibody, a virus or viral component, a receptor, a hapten, an enzyme, a hormone, a chemical compound, a pathogen, a microorganism or a component thereof, a toxin, a surface modifier, such as a surfactant to alter the surface properties or histocompatability of the nanoparticle or of an analyte when a nanoparticle associates therewith, and combinations thereof. Preferred ligands are for example, antibodies, such as monoclonal or polyclonal.

The present invention also provides a method of preparing analytes which are selectively labeled with ligated-fluorescent nanoparticles by, for example, coupling (e.g. covalently) or any other known method(s) of associating the ligated-fluorescent nanoparticles directly to the analyte (e.g., through ionic bonds, hydrogen bonds, by simple adsorption). The resulting selectively labeled analytes having a coupled or associated ligated-fluorescent nanoparticle (i.e. ligated-fluorescent nanoparticle-analyte complex) can be useful as an authentic or reference sample, for example, in a treatment method or diagnostic kit.

An "analyte" of the present invention is the object or the target of the ligated-fluorescent nanoparticle for attachment or association therewith. The analyte can be, for example, a microorganism or a component thereof, a virus or viral component, a cell or a component thereof, a biopolymer, a synthetic polymer, a synthetic material, such as a carbon nanotube, an antigen, an antibody, a receptor, a hapten, an enzyme, a hormone, a chemical compound, a pathogen, a toxin, combinations thereof, and like substances. Analytes of particular interest are microorganisms and cells, including viruses, prokaryotic and eukaryotic cells, unicellular and multi-cellular organism, e.g., fungi, bacterial, mammalian, etc., and fragments or components thereof. Other analytes of particular interest are pathogens. Monoclonal or polyclonal antibodies or other selective ligands which are part of the ligated-fluorescent nanoparticle can be linked to the surface of, for example, a pathogen.

In embodiments of the present invention there are provided methods of making a fluorescent nanoparticle, for example, comprising:

mixing a fluorescent compound, such as a reactive fluorescent dye, and an organo-silane compound, such as a co-reactive organo-silane compound, to form a fluorescent core; and mixing the resulting core with a silica forming compound, such as a tetraalkoxysilane, to form a silica shell on the core, to provide the fluorescent nanoparticle.

The methods of making the nanoparticles of the present invention can further comprise combining the resulting fluorescent nanoparticle with a ligand such as a biopolymer, a synthetic polymer, an antigen, an antibody, a microorganism, a virus, a receptor, a hapten, an enzyme, a hormone, a chemical compound, a pathogen, a toxin, a surface modifier, for example, to alter the surface or compatibility properties of the nanoparticle, combinations thereof, and like materials. The resulting combination of the fluorescent nanoparticle and a ligand provides a ligated-fluorescent nanoparticle. The methods of making the nanoparticles can also further comprise combining the resulting nanoparticle with a therapeutic agent, with or without a ligand attached to the nanoparticle. Combining the nanoparticles with a ligand or a therapeutic agent can be accomplished by, for example, coating the ligand or therapeutic agent onto the surface of the nanoparticle. Alternatively or additionally, combining a nanoparticle with a ligand or a therapeutic agent can be accomplished by, for example, imbibing the ligand or therapeutic agent into the surface of the nanoparticle. Imbibing means to assimilate or to take in or up, for example, where a porous nanoparticle surface is imbibed with a ligand, a therapeutic agent, or both. Alternatively or additionally, combining a nanoparticle with a ligand or a therapeutic agent can be accomplished by, for example, bonding the ligand or therapeutic agent to the surface of the resulting nanoparticle. Bonding includes, for example, known covalent, ionic, hydrogen, hydrophobic, coordination, adhesive, combinations thereof, and like bonding associative methods.

Because of the small size and uniformity of the nanoparticles of the present invention and their apparent solubility or high dispersibility properties, the nanoparticles can provide "molecular labels" which can readily associate with or be bonded to another entity, such as a ligand or a therapeutic agent, and thereafter be readily transported to and selectively attached to a target analyte. The selective attachment enables useful analytical detection, diagnostic, or differentiation schemes. The size of the ligated-fluorescent nanoparticles for use in embodiments of the present invention can be selected based on the number of nanoparticles to be attached to the analyte and the sensitivity of the optical or spectroscopic schemes selected.

In embodiments the present invention provides a method for monitoring movement of a cellular component of a cell comprising:

contacting the cell with a ligated-fluorescent nanoparticle to form a cell selectively decorated with the ligated-fluorescent nanoparticle; and recording the motion of a fluorescent loci for a time.

The fluorescent loci can correspond to a single ligated-fluorescent nanoparticle bound to a component of the cell. The fluorescent loci can correspond to two or more ligated-fluorescent nanoparticles bound to a component of the cell. The monitoring method enables an operator to, for example, track the diffusion of one or more fluorescent loci, such as a receptor to which a single ligated-fluorescent nanoparticle is bound, such as, in real-time or with time-lapse techniques. The ligated-fluorescent nanoparticle is preferably adapted to selectively associate with a targeted cellular component of the cell, for example, by appropriate selection of the ligand.

The cellular component can be, for example, a receptor, an antibody, a hapten, an enzyme, a hormone, a biopolymer, an antigen, a microorganism, a virUs, a pathogen, a toxin, combinations thereof, and like components. In embodiments, the ligated-fluorescent nanoparticle can be a fluorescent nanoparticle conjugated with an antibody. In embodiments, the conjugated antibody can be an immunoglobin, such as IgE.

Suitable means for detecting, recording, measuring, or imaging in embodiments of the present invention are known in the art and include, for example, a flow cytometer, a laser scanning cytometer, a fluorescence micro-plate reader, a fluorescence microscope, a confocal microscope, a bright-field microscope, a high content scanning system, and like devices.

The recording can be accomplished, for example, with a microscopically adapted camera, such as a video-microscopy camera, a digital camera, a silver halide single exposure camera, and like devices. The recording time can be any convenient and useful time period to observe notable events or phenomena, for example, intervals from about 1 microsecond to about 30 days. In typical extra-cellular, surface-cellular, or intra-cellular events, recording for a time period can be, for example, from about 1 second to about 60 minutes, more preferably from about 1 second to about 40 minutes, and even more preferably, from about 1 minute to about 30 minutes. The recording time period can often be conveniently shortened or lengthened as desired by changing the ambient temperature of the sample or system. The contacting and the recording can be accomplished in vitro using conventional microscopic photography techniques. The contacting and the recording can also be accomplished in vivo using, for example, a catheter adapted with a microscopic camera or fiber optic camera. It will be readily evident to one of ordinary skill in the art in embodiments of the present invention that "recording" can be synonymous with "detecting," since for example making a photographic recording of an illuminated specimen can also simultaneously afford detection of fluorescent loci, such as a cell or cell component selectively decorated with a ligated-fluorescent nanoparticle.

In embodiments there is provided a pharmaceutical carrier comprising the fluorescent nanoparticle of the present invention, and optionally a ligand associated with the fluorescent nanoparticle.

In embodiments there is also provided a pharmaceutical composition comprising a ligated-fluorescent nanoparticle, and a therapeutic agent associated with the fluorescent nanoparticle.

In embodiments there is provided an imaging agent comprising the ligated-fluorescent nanoparticle, for example, where the ligand of the ligated-fluorescent nanoparticle is on the surface of the nanoparticle. The imaging agent can be used in conventional imaging processes, and preferably where, for example, a high fluorescent yield or fluorescent brightness is desired. In embodiments, the ligated-fluorescent nanoparticles of the present invention can provide enhanced fluorescent brightness which is, for example, from about 2 to about 10 times greater compared to conventional surface decorated fluorescent particles, such as fluorescent latex particles.

In embodiments there is provided a method for treating a disease or disorder comprising:

administering to a patient in need of treatment an effective amount of a ligated-fluorescent nanoparticle which nanoparticle optionally includes a therapeutic agent, wherein the nanoparticle is adapted to selectively associate with a disease producing component of the cell, to form a selectively decorated cell with the ligated-fluorescent nanoparticle; and illuminating the decorated cell.

The ligated-fluorescent nanoparticle, by itself or as part of a decorated cell, when illuminated can fluoresce, heat-up, or both. Thus, the selection of the reactive fluorescent compound in preparing the fluorescent nanoparticle, and the selection of the ligand, can be made empirically depending upon the balance of fluorescent and non-fluorescent (heat dissipation) properties desired. Higher fluorescent properties may be desired where detection is paramount or difficult, for example in dilute systems. Higher non-fluorescent properties may be desired where high heating is needed to, for example, promote liberation of a therapeutic agent or to accomplish selective microscopic-cauterization or microscopic-heat therapy. In embodiments it may be desirable to use a mixture of two or more ligated-fluorescent nanoparticles having different fluorescent and non-fluorescent properties to exploit the benefits of the different properties, for example, simultaneously or sequentially, such as in the detection and treatment of a cancerous tumor.

Thus, the ligated-fluorescent nanoparticles of the present invention can be used to treat a light- or heat-sensitive diseases or disorders. Light therapy is known for activation of medicaments at one or more treatment sites within a living body. A particular embodiment of light therapy, for example, is photodynamic therapy (PDT) which is a two-step treatment process which has been found to be effective in destroying a wide variety of cancers. PDT is performed by first systemically or topically administering a photosensitizer compound or like compounds, and subsequently illuminating a treatment site with light in a waveband, which corresponds to an absorption waveband of the photosensitizer. The light energy activates the photosensitizer compound, causing it to destroy the diseased tissue, see for example, U.S. Pat. No. 6,454,789. It is readily evident to one skilled in the art that a fluorescent material, such as the ligated-fluorescent nanoparticles of the present invention, can be used in place of a photosensitizer compound.

Heat therapy methods are also known, for example, to shrink desired tissues, see U.S. Pat. No. 6,480,746, and for localized treatment of cutaneous warts, see *Arch. Dermatol*, (July 1992), vol. 128, p. 945-948, and to induce macrophage apoptosis, see U.S. Pat. No. 6,451,044. In these and related applications heat therapy can be accomplished within a body or across the skin by means of, for example, irradiation or illumination, such as ultraviolet radiation, infrared radiation, microwave radiation, etc. One of ordinary skill in the art once in possession of the present invention would readily recognize how to adapt its materials and methods to accomplish light therapy or heat therapy.

The present invention also provides a method of treatment comprising:

contacting a cell with a ligated-fluorescent nanoparticle, optionally having a therapeutic agent associated with the nanoparticle, to form a cell selectively decorated with the ligated-fluorescent nanoparticle; and irradiating the resulting decorated cell for a time.

The amount and the duration of the contacting as well as the amount and the duration of irradiating can depend on, for example, the diagnostic or therapeutic objectives of the treatment method, such as fluorescent detection of a diseased state or condition, the delivery of an effect therapeutic agent, or both. The amount and the duration of the contacting and irradiating can also depend on, for example, the relative concentration ligated-fluorescent nanoparticle to the target analyte, and the state of the cell for treatment, such as in vivo or in vitro whole cells, permeabilized cells, homogenized cells, sensitized cells, and like cell preparations.

The ligated-fluorescent nanoparticles of the present invention also have application in diagnostic kits or assays, such as immunoassays, in improved imaging agents, in purification processes, in drugs, for example, treatment regimes and therapies, such as drug delivery to specifically target and shrink tumors or to identify and separate infectious agents, and like applications.

The invention provides a kit for use in the detection of an analyte, the kit comprising a ligated-fluorescent nanoparticle, as illustrated herein.

The invention also provides a kit for detecting and monitoring a cell surface component comprising a ligated-fluorescent nanoparticle for detecting the cell surface component, and optionally a recorder for monitoring the cell surface component.

The aforementioned kits include packaging of the kit component(s) and instructions for use of the kit.

The invention also provides an assay method for detecting motion or a change in the location of a cellular component in, or on the surface of, a cell when the cell is treated with a therapeutic agent comprising:

contacting a cell with a ligated-fluorescent nanoparticle, wherein the nanoparticle includes a therapeutic agent, to bind the ligated-fluorescent nanoparticle to a cellular component; and recording the fluorescent signal, such as from one or more fluorescent loci, and determining the relative motion or a change in the location of a targeted cellular component.

The motion or movement of the fluorescent loci, that is an analyte bound by a ligated-fluorescent nanoparticle, is representative of and can be correlated to the motion or movement of the bound analyte, such as a cellular component.

The assay method for detecting motion or a change in the location of a cellular component can include, for example, optionally mapping or plotting the recorded positions of ligated-fluorescent nanoparticle. The assay method can further comprise determining the difference between the motion or movement of the analyte bound ligated-fluorescent nanoparticle in the presence and absence of the therapeutic agent, for example, in a tandem or control experimental design.

The nanoparticles materials, such as the ligated-fluorescent nanoparticles, and methods of use of the present invention can be used as, for example, labeled assay reagents or reagent products made therefrom, for assaying the presence of a cell component, for example, an enzyme, a receptor, and like cell components. The location of the cell component can be detected and determined, for example, inside a metabolically active whole cell, in a whole cell lysate, in a permeabilized cell, in a fixed cell, or with a partially purified cell component in a cell-free environment. The ligated-fluorescent nanoparticle contains an associated ligand or ligator, such as an antibody, which nanoparticle targets or associates with a specific cell component of interest. The ligated-fluorescent nanoparticle also contains a fluorescent label or fluorescent component in the nanoparticle core, which fluorescent component marks or reports on the presence of the target cell component when the nanoparticle and the target cell component are associated and appropriately illuminated or irradiated.

The invention also provides methods for treating a disease by administration of an effective amount of a linked fluorescent nanoparticles. The methods may involve administration of a linked fluorescent nanoparticles as described herein, alone, in a pharmaceutical composition, or in combination with other therapeutic agents or pharmaceutical compositions.

The invention also provides methods to increase the effectiveness of a therapeutic agent by linking the therapeutic agent to a fluorescent nanoparticle. The fluorescent nanoparticles and pharmaceutical compositions thereof may also be used to associate therapeutic agents to increase the therapeutic efficiency of the therapeutic agent. Conjugation of a fluorescent nanoparticle with a ligand to form a linked- or ligated-fluorescent nanoparticle is preferably accomplished in vitro where, for example, ligand amounts and conditions can be carefully controlled to produce a product of high purity and high quality. Similarly, modifying the linked fluorescent nanoparticle with a therapeutic agent is preferably accomplished in vitro.

The present invention provides fluorescent nanoparticles and ligated-fluorescent nanoparticle thereof, and methods for their use in, for example, immuno-labeling, sub-cellular recognition procedures, diagnostics, or cell sorting. The methods of the present invention provide advantages which overcome shortcomings of known methodologies and as illustrated herein.

The present invention provides ligated-fluorescent nanoparticles which are highly dispersible, and are useful, for example, in improved methods for chemical and biochemical analysis, such as, the detection of biological analytes including micro-organisms or sub-cellular components. The ligated-fluorescent nanoparticle can provide high local concentrations of fluorescent material because of their high target selectively or affinity, and because of their enhanced brightness compared to known fluorescent particles. The fluorescent material is present throughout the nanoparticle core and not simply as a surface coating material as in many conventional materials.

A "therapeutic agent" is a substance that may be used in the diagnosis, cure, mitigation, treatment, or prevention of disease in a human or another animal. Such therapeutic agents include substances recognized in the official United States Pharmacopeia, official Homeopathic Pharmacopeia of the United States, official National Formulary, or any supplement thereof.

Therapeutic agents that can be incorporated with the fluorescent nanoparticles or the ligated-fluorescent nanoparticles of the invention include nucleosides, nucleoside analogs, oligopeptides, polypeptides, COX-2 inhibitors, apoptosis promoters, urinary tract agents, vaginal agents, vasodilators neurodegenerative agents (e.g., Parkinson's disease), obesity agents, ophthalmic agents, osteoporosis agents, para-sympatholytics, para-sympathometics, anti-anesthetics, prostaglandins, psychotherapeutic agents, respiratory agents, sedatives, hypnotics, skin and mucous membrane agents, antibacterials, anti-fungals, anti-neoplastics, cardioprotective agents, cardiovascular agents, anti-thrombotics, central nervous system stimulants, cholinesterase inhibitors, contraceptives, dopamine receptor agonists, erectile dysfunction agents, fertility agents, gastrointestinal agents, gout agents, hormones, immunomodulators, suitably functionalized analgesics or general or local anesthetics, anti-convulsants, anti-diabetic agents, anti-fibrotic agents, anti-infectives, motion sickness agents, muscle relaxants, immuno-suppresives, migraine agents, non-steroidal anti-inflammatory drugs (NSAIDs), smoking cessation agents, or sympatholytics (see Physicians' Desk Reference, 55th ed., 2001, Medical Economics Company, Inc., Montvale, N.J., pages 201-202).

Examples of specific therapeutic agents that can be linked, ligated, or associated with the fluorescent nanoparticles of the invention are flomoxef; fortimicin(s); gentamicin(s); glucosulfone solasulfone; gramicidin S; gramicidin(s); grepafloxacin; guamecycline; hetacillin; isepamicin; josamycin; kanamycin(s); flomoxef; fortimicin(s); gentamicin(s); glucosulfone solasulfone; gramicidin S; gramicidin(s); grepafloxacin; guamecycline; hetacillin; isepamicin; josamycin; kanamycin(s); bacitracin; bambermycin(s); biapenem; brodimoprim; butirosin; capreomycin; carbenicillin; carbomycin; carumonam; cefadroxil; cefamandole; cefatrizine; cetbuperazone; cefclidin; cefdinir; cefditoren; cefepime; cefetamet; cefixime; cefmenoxime; cefminox; cladribine; apalcillin; apicycline; apramycin; arbekacin; aspoxicillin; azidamfenicol; aztreonam; cefodizime; cefonicid; cefoperazone; cefloranide; cefotaxime; cefotetan; cefotiam; cefozopran; cefpimizole; cefpiramide; cefpirome; cefprozil; cefroxadine; cefteram; ceftibuten; cefuzonam; cephalexin; cephaloglycin; cephalosporin C; cephradine; chloramphenicol; chlortetracycline; clinafloxacin; clindamycin; clomocycline; colistin; cyclacillin; dapsone; demeclocycline; diathymosulfone; dibekacin; dihydrostreptomycin; 6-mercaptopurine; thioguanine; capecitabine; docetaxel; etoposide; gemcitabine; topotecan; vinorelbine; vincristine; vinblastine; teniposide; melphalan; methotrexate; 2-p-sulfanilylanilinoethanol; 4,4'-sulfinyldianiline; 4-sulfanilamidosalicylic acid; butorphanol; nalbuphine, streptozocin; doxorubicin; daunorubicin; plicamycin; idarubicin; mitomycin C; pentostatin; mitoxantrone; cytarabine; fludarabine phosphate; butorphanol; nalbuphine, streptozocin; doxorubicin; daunorubicin; plicamycin; idarubicin; mitomycin C; pentostatin; mitoxantrone; cytarabine; fludarabine phosphate; acediasulfone; acetosulfone; amikacin; amphotericin B; ampicillin; atorvastatin; enalapril; ranitidine; ciprofloxacin; pravastatin; clarithromycin; cyclosporin; famotidine; leuprolide; acyclovir; paclitaxel; azithromycin; lamivudine; budesonide; albuterol; indinavir; metformin; alendronate; nizatidine; zidovudine; carboplatin; metoprolol; amoxicillin; diclofenac; lisinopril; ceftriaxone; captopril; salmeterol; xinafoate; imipenem; cilastatin; benazepril; cefaclor; ceftazidime; morphine; dopamine; bialamicol; fluvastatin; phenamidine; podophyllinic acid 2-ethylhydrazine; acriflavine; chloroazodin; arsphenamine; amicarbilide; aminoquinuride; quinapril; oxymorphone; buprenorphine; floxuridine; dirithromycin; doxycycline; enoxacin; enviomycin; epicillin; erythromycin; leucomycin(s); lincomycin; lomefloxacin; lucensomycin; lymecycline; meclocycline; meropenem; methacycline; micronomicin; midecamycin(s); minocycline; moxalactam; mupirocin; nadifloxacin; natamycin; neomycin; netilmicin; norfloxacin; oleandomycin; oxytetracycline; p-sulfanilylbenzylamine; panipenem; paromomycin; pazufloxacin; penicillin N; pipacycline; pipemidic acid; polymyxin; primycin; quinacillin; ribostamycin; rifamide; rifampin; rifamycin SV; rifapentine; rifaximin; ristocetin; ritipenem; rokitamycin; rolitetracycline; rosaramycin; roxithromycin; salazosulfadimidine; sancycline; sisomicin; sparfloxacin; spectinomycin; spiramycin; streptomycin; succisulfone; sulfachrysoidine; sulfaloxic acid; sulfamidochrysoidine; sulfanilic acid; sulfoxone; teicoplanin; temafloxacin; temocillin; tetroxoprim; thiamphenicol; thiazolsulfone; thiostrepton; ticarcillin; tigemonam; tobramycin; tosufloxacin; trimethoprim; trospectomycin; trovafloxacin; tuberactinomycin; vancomycin; azaserine; candicidin(s); chlorphenesin; dermostatin(s); filipin; fungichromin; mepaitricin; nystatin; oligomycin(s); perimycin A; tubercidin; 6-azauridine; 6-diazo-5-oxo-L-norleucine; aclacinomycin(s); ancitabine; anthramycin; azacitadine; azaserine; bleomycin(s); ethyl biscoumacetate; ethylidene dicoumarol; iloprost; lamifiban; taprostene; tioclomarol; tirofiban; amiprilose; bucillamine; gusperimus; gentisic acid; glucamethacin; glycol salicylate; meclofenamic acid; mefenamic acid; mesalamine; niflumic acid; olsalazine; oxaceprol; S-enosylmethionine; salicylic acid; salsalate; sulfasalazine; tolfenamic acid; carubicin; carzinophillin A; chlorozotocin; chromomycin(s); denopterin; doxifluridine; edatrexate; eflornithine; elliptinium; enocitabine; epirubicin; mannomustine; menogaril; mitobronitol; mitolactol; mopidamol; mycophenolic acid; nogalamycin; olivomycin(s); peplomycin; pirarubicin; piritrexim; prednimustine; procarbazine; pteropterin; puromycin; ranimustine; streptonigrin; thiamiprine; mycophenolic acid; procodazole; romurtide; sirolimus (rapamycin); tacrolimus; butethamine; fenalcomine; hydroxytetracaine; naepaine; orthocaine; piridocaine; salicyl alcohol; 3-amino-4-hydroxybutyric acid; aceclofenac; alminoprofen; amfenac; bromfenac; bromosaligenin; bumadizon; carprofen; diclofenac; diflunisal; ditazol; enfenamic acid; etodolac; etofenamate; fendosal; fepradinol; flufenamic acid; Tomudex® (N-[[5-[[(1,4-Dihydro-2-methyl-4-oxo-6-quinazolinyl)methyl]methylamino]-2-thienyl] carbonyl]-L-glutamic acid), trimetrexate, tubercidin, ubenimex, vindesine, zorubicin; argatroban; coumetarol or dicoumarol.

Lists of additional therapeutic agents can be found, for example, in: Physicians' Desk Reference, 55th ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12th ed., 1996, Merck & Co., Inc., Whitehouse Station, N.J.

It will be readily appreciated by those skilled in the art how to determine, for example, therapeutic activity using standard tests or other similar tests which are known in the art.

A "pharmaceutical composition" includes a therapeutic agent as exemplified herein in combination with a fluorescent nanoparticle of the invention, for example, where the fluorescent nanoparticle can act as the pharmaceutically acceptable carrier. A pharmaceutical composition of the present invention, in addition to a therapeutic agent combination with a fluorescent nanoparticle, can be formulated into or with other acceptable carriers or dosage forms, such as, a solid, gelled or liquid diluent or an ingestible capsule. The pharmaceutical compositions of the invention, the salts thereof, or a mixture thereof, may be administered orally in the form of a suitable pharmaceutical unit dosage form. The pharmaceutical compositions of the invention may be prepared in many forms that include tablets, hard or soft gelatin capsules, aqueous solutions, suspensions, and liposomes and other slow-release formulations, such as shaped polymeric gels.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The nanoparticle pharmaceutical compositions of the invention may also be formulated for parenteral administration (e.g., by injection, for example, bolus injection or continuous infusion) and may be presented in unit dosage form in ampules, pre-filled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the pharmaceutical compositions of the invention may be in powder form, obtained by aseptic isolation of sterile solid or by lyophilization from solution, for constitution with a suitable vehicle, e.g., sterile, pyrogen-free water, before use.

For topical administration to the epidermis, the pharmaceutical compositions may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506; and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The pharmaceutical compositions can also be delivered via ionophoresis, e.g., as disclosed in U.S. Pat. Nos. 4,140,122; 4,383,529; or 4,051,842.

Pharmaceutical compositions suitable for topical administration in the mouth include unit dosage forms such as lozenges comprising a pharmaceutical composition of the invention in a flavored base, usually sucrose and acadia or tragacanth; pastilles comprising the pharmaceutical composition in an inert base such as gelatin and glycerin or sucrose and acacia; mucoadherent gels, and mouthwashes comprising the pharmaceutical composition in a suitable liquid carrier.

For topical administration to the eye, the pharmaceutical compositions can be administered as drops, gels (S. Chrai et al., U.S. Pat. No. 4,255,415), gums (S. L. Lin et al., U.S. Pat. No. 4,136,177) or via a prolonged-release ocular insert (A. S. Michaels, U.S. Pat. No. 3,867,519 and H. M. Haddad et al., U.S. Pat. No. 3,870,791).

When desired, the above-described pharmaceutical compositions can be adapted to give sustained release of a therapeutic compound employed, e.g., by combination with certain hydrophilic polymer matrices, e.g., comprising natural gels, synthetic polymer gels or mixtures thereof.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the pharmaceutical composition with the softened or melted carrier(s) followed by chilling and shaping in molds.

Pharmaceutical compositions suitable for vaginal administration may be presented as pessaries, tampons, creams, gels, pastes, foams or sprays containing, in addition to the nanoparticles and the therapeutic agent, such carriers are well known in the art.

For administration by inhalation, the pharmaceutical compositions according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the pharmaceutical compositions of the invention may take the form of a dry powder composition, for example, a powder mix of the pharmaceutical composition and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the pharmaceutical compositions of the invention may be administered via a liquid spray, such as via a plastic bottle atomizer. Typical of these are the Mistometer® (isoproterenol inhaler—Wintrop) and the Medihaler® (isoproterenol inhaler—Riker).

Pharmaceutical compositions of the invention may also contain other adjuvants such as flavorings, colorings, antimicrobial agents, or preservatives.

It will be further appreciated that the amount of the pharmaceutical compositions required for use in treatment will vary not only with the particular salt selected but also with the route of administration, the nature of the condition being treated and the age and condition of the patient and will be ultimately at the discretion of the attendant physician or clinician.

The amount of a therapeutic agent in combination with ligated-fluorescent nanoparticles of the invention which can be administered and the frequency of administration to a given human patient will depend upon a variety of variables related to the patient's psychological profile and physical condition. For evaluations of these factors, see J. F. Brien et al., *Europ. J. Clin. PharinacoL*, 14, 133 (1978); and *Physicians' Desk Reference*, Charles E. Baker, Jr., Pub., *Medical Economics Co.*, Oradell, N.J. (41st ed., 1987). Generally, the dosages of the therapeutic agent when used in combination with the ligated-fluorescent nanoparticles of the present can be lower than when the therapeutic agent is administered alone or in conventional pharmaceutical dosage forms. The high specificity of the ligated-fluorescent nanoparticle for a target site, such as a receptor situated on a cell's surface, can provide relatively high localized concentrations of a therapeutic agent, or alternatively, a sustained release of a therapeutic agent over an extended time period.

"Pharmaceutically acceptable salts" of the ligated-fluorescent nanoparticles and the therapeutic agents of the invention can include, but are not limited to, the nontoxic addition salts with organic and inorganic acids, such as the citrates, bicarbonates, malonates, tartrates, gluconates, hydrochlorides, sulfates, phosphates, and like salts. Additionally, in cases where the nanoparticles are sufficiently basic or acidic to form stable acid or base salts, preparation of the nanoparticles as salts may be appropriate. Examples of acceptable salts are organic acid addition salts formed with acids which form a acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Acceptable salts may be obtained using standard procedures known in the art, for example by reacting a sufficiently basic compound such as an amine with a suitable acid affording a diagnostically acceptable anion. Alkali metal (e.g., sodium, potassium or lithium) or alkaline earth metal (e.g. calcium) salts of carboxylic acids can also be made.

"Receptor" is any macromolecular compound or composition capable of recognizing (e.g. such as having an enhanced binding affinity to) a particular spatial and polar organization of a molecule, i.e., epitopic or determinant site. Illustrative receptors include naturally occurring receptors, e.g., thyroxine binding globulin, antibodies, enzymes, immunoglobulin (Fab) fragments, lectins, various proteins found on the surface of cells (cluster of differentiation or CD molecules), and the like. CD molecules denote known and unknown proteins on the surface of eukaryotic cells, for example, CD4 is the molecule that primarily defines helper T lymphocytes.

"Haptens" can include naturally occurring hormones, naturally occurring drugs, synthetic drugs, pollutants, allergens, affector molecules, growth factors, chemokines, cytokines, lymphokines, amino acids, oligopeptides, chemical intermediates, nucleotides, oligonucleotides, and the like. The use for such compounds may be in the detection of drugs of abuse, therapeutic dosage monitoring, health status, donor matching for transplantation purposes, pregnancy (e.g., hCG or alpha-fetoprotein), detection of disease, e.g. endotoxins, cancer antigens, pathogens, and the like.

"Immunoconjugate" is a molecule formed by attachment of two different molecules or entities, such as an antibody ligated to a fluorescent nanoparticle, and a second usually biologically active molecular entity (analyte) such as an organic drug molecule, a radionuclide, an enzyme, a toxin, a protein, and like materials that can be conjugated to the antibody to form the conjugate. The antibody portion directs or guides the attached fluorescent nanoparticle to the target analyte enabling the fluorescent nanoparticle to efficiently produce a biological or marking effect.

Pathogens of interest can be, for example, viruses such as Herpesviruses, Poxviruses, Togaviruses, Orthomyxoviruses, Paramyxoviruses, Rhabdoviruses, Coronaviruses, Arenaviruses, and Retroviruses. Pathogens also include prions and bacteria including but not limited to *Escherichia coli*, *Pseudomonas aeruginosa, Enterobacter cloacae, Staphylococcus aureus, Enterococcus faecalis, Klebsiella pneumoniae, Salmonella typhimurium, Staphylococcus epidermidis, Serratia marcescens, Mycobacterium bovis*, methicillin resistant *Staphylococcus aureus* and *Proteus vulgaris*. A non-exhaustive list of these organisms and associated diseases can be found, for example, in U.S. Pat. No. 5,795,158.

Assays using nanoparticles of the invention can be carried out in a biological fluid, including separated or unfiltered biological fluids such as urine, cerebrospinal fluid, pleural fluid, synovial fluid, peritoneal fluid, amniotic fluid, gastric fluid, blood, serum, plasma, lymph fluid, interstitial fluid, tissue homogenate, cell extracts, saliva, sputum, stool, physiological secretions, tears, mucus, sweat, milk, semen, vaginal secretions, fluid from ulcers and other surface eruptions, blisters, abscesses, and extracts of tissues including biopsies of normal, malignant, and suspect tissues or any other constituents of the body which may contain the analyte of interest. Other similar specimens such as cell or tissue culture or culture broth are also of interest. Alternatively, the sample can be obtained from an environmental source, such as soil, water, or air; or from an industrial source such as taken from a waste stream, a water source, a supply line, or a production lot. Industrial sources also include fermentation media, such as from a biological reactor or food fermentation process such as brewing; or foodstuff, such as meat, game, produce, or dairy products. The test sample can be pre-treated prior to use, such as preparing plasma from blood, diluting viscous fluids, and the like; methods of pre-treatment can involve filtration, fractionation, distillation, concentration, inactivation of interfering compounds, and addition of reagents, and like steps, or combinations thereof.

Methods for detecting multiple subpopulations of analytes are known, see for example, U.S. Pat. No. 5,567,627, to Lehnen, and can be adapted to the present invention. Methods for detecting a nucleic acid with one or more nanoparticle having oligonucleotides attached thereto, including an electrochemical assay with a probe oligonucleotide having attached a redox-active molecule, for example as in U.S. Pat. No. 6,417,340, to Mirkin, et al, can be adapted to the present invention. Methods for electrochemical detection and localization of genetic point mutations and other base-stacking perturbations within oligonucleotide duplexes adsorbed onto electrodes, such as U.S. Pat. No. 6,221,586, to Barton, et al., can be adapted to the present invention. Methods for multiplexed fluorescent analysis of a plurality of analytes in a sample, such as U.S. Pat. No. 6,268,222, to Chandler, et al., can be adapted to the present invention. Other detection methods include using ultraviolet and visible spectroscopy, see for example X. Gong and E. S. Yeung, *Anal. Chem.*, 71, 4989 (1999), "An Absorption Detection Approach for Multiplexed Capillary Electrophoresis Using a Linear Photodiode Array". Methods for separating cells using a flow through fractional cell sorting process based on the application of a magnetic force to cells having a range of magnetic labeling densities, such as U.S. Pat. No. 5,968,820, to Zborowski, et al., can be adapted to the present invention. Methods for separating particles bound to each other via non-covalent binding and agglomeration, such as U.S. Pat. No. 4,279,617, to Masson et al., can be adapted to the present invention.

For the purposes of the present invention the nanoparticle's fluorescent component should provide a signal related to the presence of analyte in the sample. Similarly, when a ligand is selected, which includes a fluorescent nanoparticle, it should provide a fluorescent signal related to the presence of analyte in the sample and which signal can be detected as electromagnetic radiation, particularly as radiation in the ultra-violet, visible or infrared range.

"Optional" or "optionally" mean that the subsequently described event or condition may but need not occur, and that the description includes instances where the event or condition occurs and instances in which it does not. For example, "optionally including" means that the named component may be present but need not be present, and the description includes situations where the named component is included and situations where the named component is not included.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

The following general methods were employed in preparing and evaluating nanoparticles, and conjugates or adducts, of the present invention.

Preparation of Fluorescent Nanoparticles

Processes and intermediates for preparing fluorescent nanoparticles of the invention are provided as further embodiments of the invention and are illustrated by the following procedures in which the meanings of the generic radicals are as given unless otherwise specified.

In embodiments, a fluorescent nanoparticle of the invention can be prepared, for example, mixing a reactive fluorescent compound, such as, a reactive fluorescent material, such as a dye (D) and a co-reactive organo-silane compound such as, a known organo-functional silane compound (OS) to form a fluorescent core particle (D-OS); and mixing the resulting core particle (D-OS) with a silica forming compound, such as a $(Si(OR)_4)$, to form a silica shell on the core which product is a fluorescent nanoparticle (D-OS)($SiO_2$).

The molar equivalent ratio of the reactive fluorescent material (D) and the co-reactive organo-silane compound (OS) can be, for example, from about 1:1 to about 1:100. The molar equivalent ratio of the fluorescent core particle (D-OS) to the silica forming compound $(Si(OR)_4)$ can be, for example, from about 1:1 to about 1:100.

The nanoparticles of the present invention can be selectively linked to either or both a ligand and analyte by, for example, any known chemical coupling reactions such as carbodiimide coupling. Other coupling methods include use of carboxylates, esters, alcohols, carbamides, aldehydes, amines, sulfur oxides, nitrogen oxides, or halides, and other methods known in the art can be used. Coupling a fluorescent nanoparticle to a ligand, or a ligated-fluorescent nanoparticle to an analyte, and like combinations, can generally be accomplished by applying the procedures and principles disclosed in U.S. Pat. No. 6,268,222, or other procedures known in the art as applied to the present invention.

In embodiments, linked-fluorescent nanoparticle, such as a surface modified fluorescent nanoparticle of the invention can be prepared, for example, from a pre-formed fluorescent nanoparticle fluorescent nanoparticle (D-OS)($SiO_2$) and a ligand, such as a biologically active compound (of formula $X_1$-$R_1$-$X_2$), and optionally a linker precursor (of formula $Z_1$-L-$Z_2$), wherein $X_1$, $X_2$, $Z_1$, and $Z_2$ can be selected from the values in the table below. In the absence of an optional linker precursor the surface silanol (Si—OH) groups of the silica shell can be used to link or associate with the ligand. The ligand and the linker precursor can be reacted or polymerized using well known synthetic techniques (e.g. by condensation) to provide a ligated-fluorescent nanoparticle or linked product of the invention. Depending on the reactive functional group ($X_1$ or $X_2$) of the ligand, a corresponding functional group ($Z_1$ or $Z_2$) can be selected from the following table, to provide an ester linkage, thioester linkage, or amide linkage in the ligated-fluorescent nanoparticle or linked product.

| Functional Group On ligand ($X_1$ or $X_2$) | Functional Group On Linker Precursor ($Z_1$ or $Z_2$) | Resulting Linkage in the Ligated-Fluorescent Nanoparticle |
|---|---|---|
| —COOH | —OH | Ester |
| —COOH | —NHR | Amide |
| —COOH | —SH | Thioester |
| —OH | —COOH | Ester |
| —SH | —COOH | Thioester |
| —NHR | —COOH | Amide |
| —$SO_3H$ | —OH | Sulfate Ester |
| —OH | —$SO_3H$ | Sulfate Ester |

As will be clear to one skilled in the art, suitable protecting groups can be used during the ligation reaction. For example, other functional groups present in the biologically active compound, on the nanoparticle surface, or the linker precursor can be partially or completely protected during ligation, and the protecting groups can subsequently be removed to provide the ligated-fluorescent nanoparticles of the invention. Suitable protecting groups and methods for their incorporation and removal are well known in the art (see for example Greene, T. W.; Wutz, P. G. M. "Protecting Groups In Organic Synthesis" second edition, 1991, New York, John Wiley & sons, Inc.).

Additionally, when a carboxylic acid is reacted with a hydroxy group, a mercapto group, or an amine group to provide an ester linkage, thioester linkage, or an amide linkage, the carboxylic acid can be activated prior to the reaction, for example, by formation of the corresponding acid chloride. Numerous methods for activating carboxylic acids, and for preparing ester linkages, thioester linkages, and amide linkages, are known in the art (see for example, *Advanced Organic Chemistry: Reaction Mechanisms and Structure*, 4th ed., Jerry March, John Wiley & Sons, pages 419-437 and 1281).

The silica shell surface of the nanoparticles can be further modified if desired by, for example, surface functionalization reactions using known cross-linking agents to afford surface functional groups and as illustrated herein. Cross-linking agents are, for example, divinyl benzene, ethylene glycol dimethacrylate, trimethylol propane trimethacrylate, N,N'-methylene-bis-acrylamide, alkyl ethers, sugars, peptides, DNA fragments, or other known functionally equivalent agents. It is readily evident to one skilled in the art that many cross-linking agents can be used in combination with, or suitable for use as the ligand in forming ligated-fluorescent nanoparticles of present invention. It is readily evident to one skilled in the art in possession of the present invention that cross-linking agents can be used in surface modifying reactions to modify the surface properties of fluorescent nanoparticles, or ligated-fluorescent nanoparticles, and as illustrated herein.

Materials and Methods

All reagents were used as received without further purification and distillation. The ammonia molarity was determined by titration with methyl blue indicator before each synthesis. Glassware was cleaned by methods described in literature and dried using a heat gun before the synthetic procedure. The volume after mixing was ignored in the molarity calculations. The amount of 3-aminopropyltriethoxysilane (APTS) in the synthesis of the fluorescent core was not taken into account in the calculations of monomer molarity in Table I.

Nanoparticle Synthesis Materials

Absolute ethanol (Aldrich), Tetrahydrofuran (Aldrich), Ammonium hydroxide (Fluka, 28%), Tetraethoxysilane (Aldrich, 98%), 3-Aminopropyltriethoxysilane (Aldrich, 99%), 3-Mercaptopropyltriethoxysilane (Gelest, 99%), Tetramethylrhodamine-5-(and-6-)-isothiocyanate *mixed isomers* (TRITC) (Molecular Probes, 88%), Alexa Fluor® 488 $C_5$ Meleimide (Molecular Probes, 97%), Alexa Flour® 488 carboxylic acid, and succinimidyl ester (Molecular Probes, ≧50%).

Preparation of Core (Fluorescent Seed) Nanoparticles Generally

Amounts of water, ammonia and solvent were measured in graduated cylinders. Fluorescent seed particle synthesis was carried out in 1 L Erlenmeyer flasks and stirred with magnetic TEFLON® coated stir bars at about 600 rpm. De-ionized water and ammonia solution were added to ethanol and stirred. About 2 mL of the reactive dye precursor in either ethanol or THF containing about 425 micromolar APTS, was added to the reaction vessel. The resulting mixture was stirred for about 1 to about 3 hours at room temperature with the reaction vessel covered with aluminum foil to minimize exposure to light to afford a fluorescent seed particle mixture. Tetrahydrofuran (THF) and absolute ethanol (EtOH) were distilled under nitrogen. Organic dyes were brought to room temperature from storage temperatures of about −20° C., then placed in a glove box.

Preparation of the Silica Shell on the Core (Fluorescent Seed) Particles Generally The silica shell coating and growth step was performed in the above mentioned fluorescent seed particle reaction mixture with regular addition of solvent, such as ethanol, methanol, or isopropanol, to prevent drastic changes in solution ionic strength while the silica forming monomer tetraethoxysilane (TEOS) was added. This prevents particle aggregation during synthesis, which can broaden the particle size distribution.

Characterization of Fluorescence Nanoparticles

The particle size and particle size distribution of the resulting fluorescent nanoparticles were characterized by electron microscopy (SEM) and fluorescence correlation spectroscopy (FCS).

Figure 1:
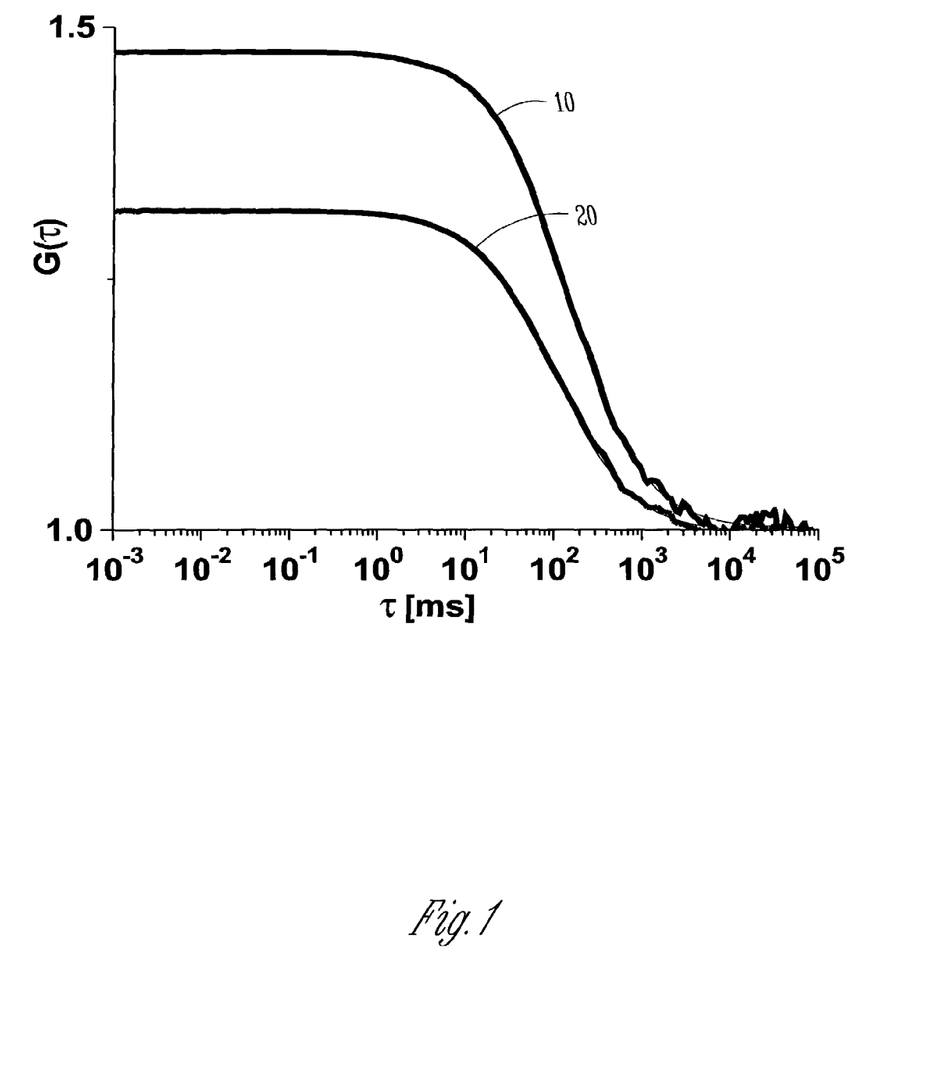
FIG. 1A illustrates an example of the fluorescent brightness of the fluorescent nanoparticles of the present invention compared to latex particles.

Referring to FIG. 1A, there is illustrated an example of fluorescent brightness properties of the fluorescent nanoparticles (10) of the present invention compared to polystyrene latex beads (20). Fluorescence correlation spectroscopy (FCS) was used to obtain the count rates for the nanoparticles and beads as follows: 100 or 300 nanometer fluorescent nanoparticles had 299.1 kHz per particle; and 300 nanometer polystyrene latex beads had 69.84 kHz per bead. Fluorescence count rates indicated that the fluorescent nanoparticles (10) were about four times brighter than the polystyrene latex beads.

Photo-physical characterizations were performed to determine: dye content per particle content, fluorescence lifetimes, and action cross-sections. The action cross-section metric is essentially the product of quantum yield and absorbance profile. Time resolved fluorescence measurements of fluorescence versus time in nanoseconds (ns) showed that a dye incorporated in a nanoparticle exhibited a longer lifetime than free dyes in solution, indicating that each dye molecule could be about 46% brighter when contained inside the core of the nanoparticles than when free in solution. For example, TRITC dyes contained within the core of the nanoparticle (with a diameter of about 25 nanometers), had a fluorescence lifetime of about 3.33 ns, compared to TRITC dyes free in solution which had a fluorescence lifetime of about 2.28 ns.

From absorbance measurements over the range of 250 to 650 nanometers it was established that there are, for example, about 20 dye molecules per nanoparticle. For example, sample R30 had about 23 TRITC dye molecules per nanoparticle; and sample R29 had about 21 TRITC dye molecules per nanoparticle. However, action cross section measurements, $\sigma_{2p}$ (GM) over the range of 700 to about 1,000 nm for two separate preparations of 25 nm particles (samples R29 and R30) demonstrated that R30 was almost twice as bright as R29 over the range and particularly at absorbance maxima at about 700 and about 840 nanometers, even though the dye content is almost identical. This observation suggested great complexity associated with interaction effects between the core and the shell and they may be responsible for the enhanced quantum efficiency observed. Thus, it is possible to further optimize the fluorescence properties of the nanoparticles of the present invention, for example, for use as biomarkers, by straight-forward procedures such as changing the thickness of the core or shell as disclosed herein. The invention will now be illustrated by the following non-limiting examples:

EXAMPLE 1

Preparation of Red Core Nanoparticles. 10 mg of tetramethylrhodamine-5-(and-6-)isothiocyanate (TRITC) were dissolved in ethanol. The molar ratio of 3-aminopropyltriethoxysilane (APTS) to TRITC was 50 to 1, with 2 mL of ethanol, per mg of APTS. Following complete dissolution of TRITC in ethanol, APTS was added to the reaction vessel. The reaction was stirred in the dark in the glove box for about 12 hours at room temperature.

EXAMPLE 2

Preparation of Green Core Nanoparticles.

5 mg of Alexa Fluor® 488 $C_5$ Meleimide was dissolved in ethanol. The molar ratio of 3-mercaptopropyltriethoxysilane (MPTS) was 100 to 1, with 2 mL of ethanol per mg of MPTS. Following complete dissolution of TRITC in ethanol, MPTS was added to the reaction vessel and stirred for about 12 hours in darkness at room temperature.

5 mg of Alexa Fluor® 488 carboxylic acid, succinimidyl ester was dissolved in THF. The molar ratio of 3-Aminopropyltriethoxysilane (APTS) to Alexa Flour® 488 carboxylic acid, succinimidyl ester was 100 to 1, with 2 ml of THF per mg of APTS. Following complete dissolution of Alexa Fluor® 488 carboxylic acid, succinimidyl ester in THF, APTS was added to the reaction vessel and stirred for 12 hours in darkness at room temperature. Due to the minute quantities, the fluorescent dye-core adducts were not isolated from the reaction medium before the silica shell was deposited.

EXAMPLE 3

Preparation of Sized Silica Coated Fluorescent Nanoparticles Preparation of silica coated fluorescent nanoparticles of different sizes was accomplished using different relative molar amounts of reagents as described above. The molar amounts of reagents for the synthesis of 20 nm to 200 nm particles are tabulated in Table I. All silica coating of fluorescent nanoparticle procedures were accomplished at ambient conditions, i.e. at room temperature with ethanol as the solvent. A representative procedure follows.

To a mixture containing fluorescent core particles there was added continuously 2 mL of TEOS in 100 mL additional solvent, dropwise such as over about 20 minutes. The remaining larger quantity of the TEOS was added at a more rapid rate, such as over about a 45 minute period with simultaneous addition of 400 mL of additional solvent. Optionally, water was added at this stage to grow particles larger than about 100 nm and to maintain the molar ratio of water to TEOS as tabulated in Table I. The resulting suspension was stirred overnight at room temperature in darkness.

TABLE I

Reactants (in molarity) for the Preparation and the Resulting Particle Size of Silica Shell Coated Fluorescent Nanoparticles

| Nominal particle size | [NH$_3$] | [H$_2$O] | [TEOS] | Solvent | Size by FCS | Size by SEM |
|---|---|---|---|---|---|---|
| 500 nm | 6.127 M | 16.83 M | 0.1923 M | i-PrOH | — | 500 nm |
| 300 nm | 6.127 M | 16.83 M | 0.1923 M | EtOH | — | 300 nm |
| 200 nm | 3.892 M | 10.80 M | 0.2443 M | EtOH | — | 200 nm |
| 100 nm | 3.892 M | 10.80 M | 0.2443 M | i-PrOH:MeOH (v:v = 3:1) | — | 125 nm |
| 70 nm | 0.0085 M | 17.60 M | 0.2003 M | EtOH | — | 75 nm |
| 50 nm | 0.0096 M | 26.68 M | 0.1518 M | MeOH | 48.6 nm | — |
| 40 nm | 0.318 M | 1.153 M | 0.155 M | EtOH | 37.6 nm | — |
| 30 nm | 0.150 M | 1.710 M | 0.155 M | EtOH | 28.8 nm | 30 nm |
| 25 nm | 0.200 M | 1.494 M | 0.155 M | EtOH | 24.4 nm | — | i-PrOH = isopropanol;
MeOH = methanol;
EtOH = ethanol
Ammonia source for of 25 nm to 40 nm and 100 nm to 500 nm was 28% ammonium hydroxide; the ammonia source for the sample nominal nanoparticle sizes 50 nm and 70 nm was 2.0 M ammonia in methanol Alternatively, to produce nanoparticles having a narrow particle size range below about 70 mm, TEOS was added in small aliquots intermittently, such as 300 microliters in about 10 to 15 minute intervals, and stirred overnight at room temperature in darkness. Molar ratio of de-ionized water to monomer was kept maintained at about at least 6-fold but not more. To better monitor water content in the reaction mixture, 2.0 M ammonia was used as the catalyst source, dissolved in ethanol, methanol or isopropanol, depending on the primary solvent of the synthesis, such as 2.0 M ammonia in ethanol. After the dye-rich core/seed particle was prepared, tetraethyl orthosilicate monomer was added intermittently, such as 300 microliters every 10 minutes to grow the siliceous shell. In contrast to the larger particle procedure where monomer was added continuously via a dropping funnel, the smaller particle size procedure (for particles below about 70 nm) the TEOS monomer was added intermittently. The alternative procedure for preparing silica shell coated fluorescent nanoparticles was devised because the size distribution of silica nanoparticles prepared by the known Stöber procedure (J. Colloid and Interface Sci., 26 62-69 (1968)) has a self-sharpening characteristic as particle size increases beyond 70 nm as more monomer is added to the reaction mixture. Thus, silica nanoparticles smaller than 70 nm generally have a much broader size distribution. Therefore, the first mentioned procedure of Example 3, was modified as described thereafter to obtain nanoparticles with a narrower size distribution than what might be expected for particle sizes in the range of about 10 to about 70 nm.

EXAMPLE 4

Nanoparticle Ligation (coupling) with IgE by Adsorption Silica coated fluorescent nanoparticles of Example 3 were diluted (1:10-1:20) with phosphate buffered saline (PBS) or Tyrodes buffer at pH 7. Immunoglobulin E (IgE) (0.85 mg/mL stock concentration) was adsorbed onto the fluorescent nanoparticles by incubating with IgE for about 3 hours at room temperature to provide, for example, nanoparticle-IgE ratios of from about 1:1 to about 1:4. For nanoparticles greater than about 50 nm, unbound IgE was removed by centrifugation. For nanoparticles of size of 50 nm or smaller, the unbound IgE was removed by adding 100 microliters (in a total volume of 500 microliters nanoparticles-IgE) of 0.25 wt % latex particles of size 1:2 microns. Unbound IgE stuck to the large latex particles which then settled out of suspension if undisturbed in several hours, for example, with overnight incubation at 4° C. The residual pellet mass was confirmed to be primarily latex particles bound with IgE and discarded. The resulting supernatant containing the IgE coupled-nanoparticle (IgE ligated-fluorescent nanoparticle) was carefully separated and placed in a vial. The resulting IgE coupled-nanoparticle samples (i.e. IgE adsorbed onto nanoparticles) were stored at 4° C. for cell binding experiments. The IgE coupled nanoparticles were diluted in Tyrodes-BSA before cell binding. The dilution was according to the IgE coupled-nanoparticle number density desired per cell.

EXAMPLE 5

Nanoparticle Surface Functionalization The surface of the nanoparticles can be further chemically modified to improve the versatility and stability of the nanoparticles, for example, introducing carboxylic acid groups or like chemical functional groups. Introducing functional groups, such as carboxylic acid groups, to the surface of silica coated nanoparticles can provide attachment points to enable covalent attachment of bio-molecules, for example, proteins and antibodies, to the surface of the nanoparticles. Surface functional groups, especially ionizable groups, provide other desirable properties to the nanoparticles, such as charge stabilization in buffered media. Charged carboxylate surface groups can maintain the nanoparticles as single particle colloidal dispersions which avoid or minimize nanoparticle agglomeration. Nanoparticle surface functionalization procedures are known and include, for example, carbodiimide modification and as illustrated herein.
Materials
3-aminopropyldimethylethoxysilane (APDMES) (Gelest Inc.); Bifunctional Cross-linking Reagent (Pierce Endogen Inc.): Methyl N-succinimidyl adipate (MSA).

Nanoparticle surface functionalization was accomplished as follows. A 20 mL suspension of nanoparticles with a diameter of 25 nm, as described in Table I, was used. The nanoparticle concentration was 4.33 mg/mL as determined by fluorescence correlation spectroscopy, and by drying and weighing known volumes of the suspension. Other nanoparticle sizes and concentrations can be surface modified according to this procedure when appropriately adapted in view of differences in particle size, surface area, concentration, and like considerations.

Fluorescent nanoparticles having a silica shell were cleaned by dialysis after their initial preparation described above. The concentration of the silica shelled nanoparticle suspension was determined by drying aliquots of the nanoparticle suspension in a vacuum oven and weighing, or by fluorescence correlation spectroscopy. Assuming a density of 2 g/mL and knowing the size of the nanoparticles, the number of particles per mL of suspension was calculated to be about $1.78 \times 10^{16}$. The total nanoparticle surface area, assuming solid particles, was for example, about $3.35 \times 10^{19}$ nm$^2$. The density of silanol groups can be estimated as about 1.4 —OH groups per square nanometer according to literature values (e.g. R. Iler, *The Chemistry of Silica*), and hence there is about $7.78 \cdot 10^{-5}$ moles of —OH groups available for reaction with APDMES for 100% amine coverage. APDMES was added in a 2 molar excess with about 5 mg of ammonium fluoride as a catalyst, and allowed to react for about 12 hours at ambient temperature and shielded from ambient light. Excess unreacted APDMES was dialyzed away in phosphate buffer at pH 7 over 12 hours. The resulting aminated nanoparticles suspended in phosphate buffer pH 7 were then reacted with 2-molar excess of MSA dissolved in dimethyl sulfoxide at ambient temperature for about 2 to 6 hours. Excess unreacted MSA was dialyzed away in phosphate buffer at pH 9.5 for about 6 to 12 hours, which also hydrolyzes the ester group in the MSA, to afford carboxylic acid groups covalently attached to the surface of the nanoparticle.
Nanoparticle Characterization by FTIR
The nanoparticle products at each functionalization step described above were characterized by Fourier Transform Infra-Red (FTIR) spectroscopy. The vibration bands of the mono-substituted amide groups at 1500-1600 cm$^{-1}$ indicated the linkage between amine groups of the silane compound APDMES and the succinimidyl ester groups of the MSA compound, as well as the carboxylic acid signature at 1700 cm$^{-1}$. The observed spectroscopic changes compared to the starting nanoparticles were indicative of successful surface functionalization reactions.

EXAMPLE 6

Nanoparticle Ligation (coupling) by Covalent Conjugation Other surface functionalization examples can be accomplished by covalent conjugation of fluorescent nanoparticles with various biomolecules as described above.

EXAMPLE 7

Cell Binding with IgE Coupled-Fluorescent Nanoparticles Specificity binding experiments using a rat basophilic leukemia (RBL) mast cell model system demonstrated specific binding characteristics of the fluorescent silica-based nanoparticles. Cells (e.g. rat basophilic leukemia (RBL) mast cells) were harvested using Trypsin-EDTA. The cells were then counted to determine the cell concentration (number of cells per mL). The appropriate number of cells was incubated with IgE coupled-nanoparticles, for example, around $2 \times 10^5$ IgE coupled-nanoparticles per cell, for about 1 hour on ice to avoid any internalization. The resulting nanoparticle-IgE bound cells, i.e. IgE coupled-nanoparticles bound to cells, were washed with Tyrodes-BSA, and the cells were viewed under a confocal microscope for specific binding.

Confocal microscope images showed, for example, the top surface of the cells decorated with the red nanoparticles, and the antibody IgE is labeled with a green fluorophore to show co-localization of the antibody with the nanoparticles. Another set of images, taken from the equitorial view of the cells showed an alternative confocal view where diffusive motions of the antibody receptors marked by the fluorescent nanoparticles can be monitored via SPT. Appropriate controls were performed to check for non-specific binding as follows. Control cells were pre-sensitized overnight using IgE, so that all the receptor sites were blocked. These blocked cells were then harvested in the same manner as above using Trypsin-EDTA, labeled with same IgE coupled-nanoparticles per cell concentration. These cells were then viewed under the confocal microscope for any nonspecific binding (or sticking).

Figure 2A:
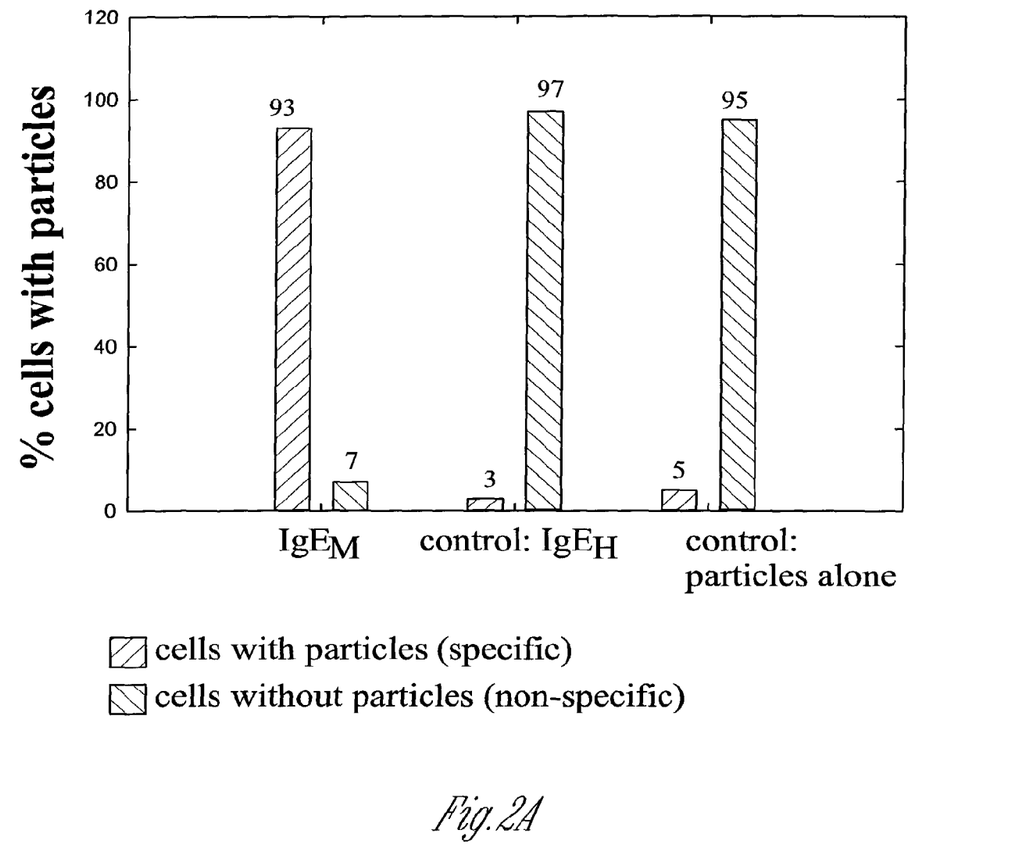
FIG. 2A illustrates an example of bio-molecule binding specificity of the fluorescent nanoparticles of the present invention.
Figure 2B:
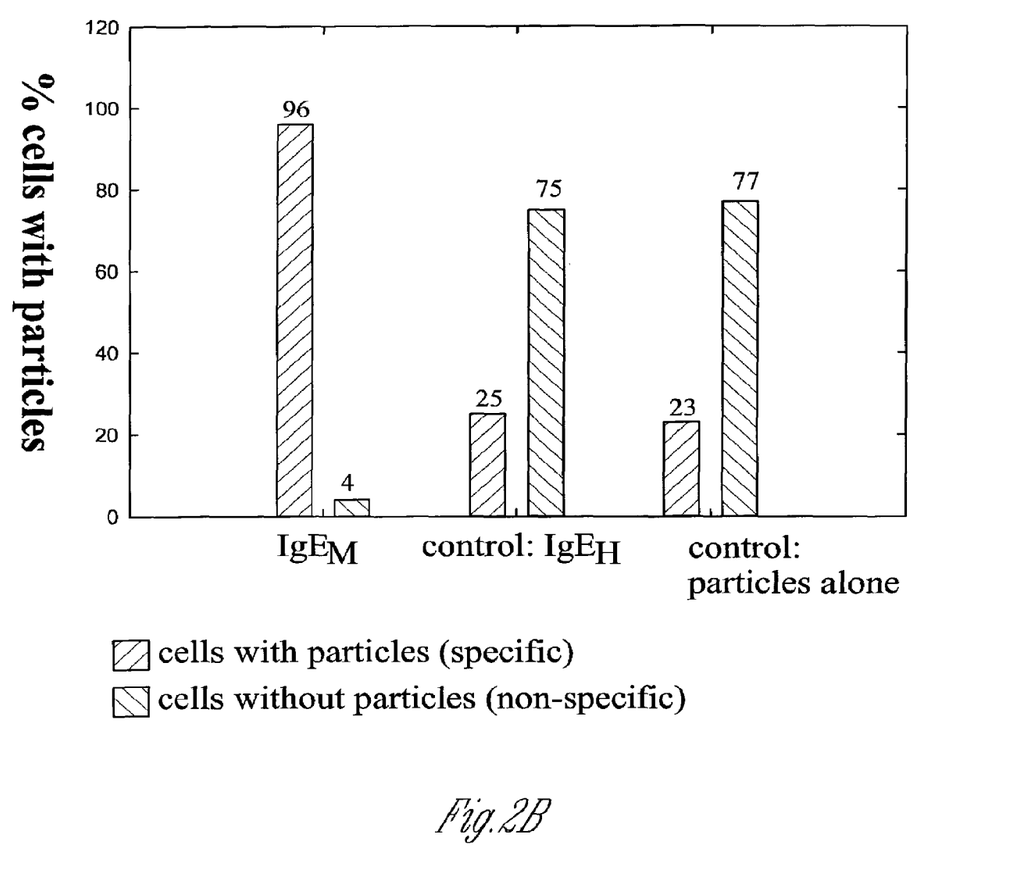
FIG. 2B illustrates an example of bio-molecule binding specificity of comparative latex particles.

Referring to FIGS. 2A and 2B, there is illustrated an example of high bio-molecular binding specificity of, for example, 100 or 300 nanometer diameter fluorescent nanoparticles of the present invention (FIG. 2A) compared to polystyrene latex beads (FIG. 2B) as measured by cell counting statistics. The result indicate that specific interactions (represented by the left-side of the bar pairs) of rat basophilic leukemia (RBL) mast cells coupled with IgE coupled-nanoparticles and cells coupled with polystyrene latex beads are comparable whereas less desirable or undesired non-specific interactions (represented by the right-side of the bar pairs), such as "sticking" interactions, were greater for polystyrene latex beads and cells compared to IgE coupled-nanoparticles and cells. A comparable result is expected for fluorescent nanoparticles of the present invention with diameters between 25 and 100 nanometers.

In FIGS. 2A and 2B, the legends:

"$IgE_M$" refers to mouse IgE which will bind specifically to IgE receptors of rat basophilic leukemia (RBL) mast cells;

"control: $IgE_H$" refers to human IgE which will not bind to IgE receptors of the aforementioned rat cells; and "control: particles alone" refers to the respective binding of IgE coupled-fluorescent nanoparticles with cells, and binding of polystyrene latex beads with cells.

EXAMPLE 8

Single Particle Tracking (SPT) Single fluorescent nanoparticle tracking experiments were performed by confocally following the motion of a selected single bright fluorescent spot (corresponding to a single receptor bound particle) for about 20-30 minutes to track the diffusion of the receptor to which the single particle was bound. Alternatively, a plurality of selected single bright fluorescent spots could be tracked.

Single particle tracking evaluates lateral diffusion of individual components on cell surfaces. This method is based on direct observation of bright fluorescent probes that are specifically conjugated to macromolecules of interest. Tracking of individual components reveals a variety of interesting and useful behaviors including confinement to a small region or movement along a track. This information enables an understanding of how components interact within cells, on cell membranes and like structures or components. However, the method is highly dependent on the quality of the probes. A significant shortcoming of the method has been nonspecific binding of the particles to cells. The fluorescent nanoparticles and the ligated-fluorescent nanoparticles of the present invention provide enhanced brightness and high conjugation specificity to a component of interest. The ligated-fluorescent nanoparticles were demonstrated to be biocompatible and minimize non-specific binding interactions.

EXAMPLE 9

Mesoporous Silica Nanoparticles for Targeted Delivery and Controlled Release of a Therapeutic Agent Fluorescent core nanoparticles were prepared according to, for example, Examples 1 and 2, and in accord with the general core preparative procedure above.

Mesoporous Shell

A surface substantive agent, N-hexadecyltrimethylammonium bromide (2.4 g, 6.6 mmol, HDTB), was dissolved in the reaction mixture containing fluorescent seed core nanoparticles. The mixture was stirred (450 rpm) until the HDTB was fully dissolved and then 3.4 g TEOS (16 mmol) was added all at once. The HDTB serves as a templating agent around which the silica shell's formation is ordered and perturbed to enable pore formation by subsequent removal of the HDTB associated with the surface. Subsequent cleaning or removal of the HDTB from the nanoparticle provides fluorescent nanoparticles having a mesoporous silica shell.

Cleaning Procedure

After about 5 hours of reaction with TEOS, a solid was recovered from three centrifugation washes at 6,000 rpm. At each centrifugation step the supernatant was refreshed with absolute ethanol. Two washes by filtration in de-ionized water followed the centrifugation procedure. The centrifugation and filtration steps removed approximately 90% of the HDTB surfactant. The recovered nanoparticles containing solid was finally suspended in absolute ethanol. The suspension was homogenized by ultrasonic agitation.

A vacuum distillation was carried out to exchange ethanol solvent with dimethyl sulfoxide (DMSO). Final concentrations were determined by drying an aliquot of the suspension and weighing the solid mass. The resulting mesoporous nanoparticles in DMSO were suitable for loading therapeutic agent as illustrated below.

Loading Mesoporous Nanoparticles with a Therapeutic Agent

The above mesoporous nanoparticles suspended in DMSO were stirred and transferred to a 50 mL Falcon tube. The solution was centrifuged at 3,000 rpm for about 5 minutes and the volume of DMSO was reduced to 4 mL by pouring off 6 mL of the supernatant fluid. A 16 mg sample of a therapeutic agent, camptothecin (CPT), was added to the solution. After 5 hours, the solution was centrifuged, and two washes with phosphate buffer saline (PBS) were done. For each wash, 20 mL of PBS was added, and the particles were sonicated and centrifuged. Sonication was done at 15% power with a pulse rate of 1.0 second on and 1.0 second off for 30 seconds of pulsing or until the solution appeared homogenous. The centrifugation was done at 25° C. at 3,000 rpm for 5 minutes. Therapeutic agent loaded particles were stored at room temperature.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for detecting the presence of an analyte comprising:

contacting a sample which may contain an analyte with a fluorescent nanoparticle conjugated to a ligand, which ligand is adapted to associate with the analyte, if present, to form a fluorescent nanoparticle-ligand-analyte complex, wherein the fluorescent nanoparticle comprises a silica-based core and a silica shell on the silica-based core, wherein the silica-based core comprises an organic functional group comprising a mercapto substituent and an organic fluorescent compound throughout the silica-based core, and wherein the fluorescent nanoparticle has a diameter of 70 nm or less; and detecting at least one fluorescent signal from the fluorescent nanoparticle-ligand analyte complex to establish the presence of the analyte.

2. The method of claim 1 wherein the ligand comprises at least one of a polymer or an oligomer selected from the group consisting of a cell component, a biopolymer, a synthetic polymer, an antigen, an antibody, a receptor, a hapten, an enzyme, a hormone, a chemical compound, a pathogen, a toxin, and combinations thereof; and wherein the analyte is selected from the group consisting of a microorganism, a virus, a cell, a cell component, a biopolymer, a synthetic polymer, an antigen, an antibody, a receptor, a hapten, an enzyme, a hormone, a chemical compound, a pathogen, a toxin, and combinations thereof.

3. The method of claim 1, wherein the fluorescent nanoparticle is conjugated to the ligand through covalent bonding.

4. The method of claim 1, wherein the ligand comprises at least one of a protein, a peptide, or an oligopeptide.

5. The method of claim 1, wherein the ligand is conjugated to the nanoparticle by a coupling agent comprising at least one carbon containing linkage, the carbon containing linkage selected from the group comprising an ester linkage, a thioester linkage, an amide linkage, a sulfate ester linkage and combinations thereof.

6. The method of claim 1 wherein the silica shell covers from about 10 percent to about 100 percent of the surface area of the core.

7. The method of claim 1, wherein the ligand is crosslinked to a second ligand, wherein the second ligand is conjugated to the fluorescent nanoparticle.

8. The method of claim 1, wherein the mercapto substituent is conjugated to a fluorescent material.

9. A method for detecting the presence of an analyte comprising:

contacting a sample that may contain an analyte with a fluorescent nanoparticle wherein the fluorescent nanoparticle has a diameter of 70 nm or less, the fluorescent nanoparticle conjugated to a ligand, which ligand is adapted to associate with the analyte, if present, to form a fluorescent nanoparticle-ligand-analyte complex, wherein the fluorescent nanoparticle comprises a silica-based core and a silica shell on the silica-based core, wherein the silica-based core comprises an organic functional group comprising a mercapto substituent and an organic fluorescent compound throughout the silica-based core, and wherein the fluorescent nanoparticle is conjugated to the ligand through covalent bonding with a linker comprising two organic functional groups, one organic functional group conjugated to the silica shell and the other organic functional group conjugated to the ligand; and detecting at least one fluorescent signal from the fluorescent nanoparticle-ligand-analyte complex to establish the presence of the analyte.

10. The method of claim 9, wherein the silica-based core further comprises a silica-based network, wherein the fluorescent compound is covalently attached to the silica-based network.

* * * * *